United States Patent [19]

Blake, III et al.

[11] Patent Number: 4,702,247

[45] Date of Patent: Oct. 27, 1987

[54] LIGATING CLIP

[75] Inventors: Joseph W. Blake, III, New Canaan, Conn.; Jack W. Kaufman, Merrick, N.Y.

[73] Assignee: American Hospital Supply Corporation, Evanston, Ill.

[21] Appl. No.: 767,472

[22] Filed: Aug. 20, 1985

[51] Int. Cl.⁴ ............................................. A61B 17/12
[52] U.S. Cl. ..................................... 128/325; 128/346
[58] Field of Search ......................... 128/325, 325, 346

[56] References Cited

U.S. PATENT DOCUMENTS

| | | | |
|---|---|---|---|
| 3,363,628 | 1/1968 | Wood | 128/325 |
| 4,188,953 | 2/1980 | Klieman et al. | 128/346 |
| 4,212,303 | 7/1980 | Nolan | 128/346 |
| 4,394,864 | 7/1983 | Sandhaus | 128/325 |

*Primary Examiner*—Paul J. Hirsch

*Attorney, Agent, or Firm*—Roger A. Williams; Paul C. Flattery; Robert E. Hartenberger

[57] ABSTRACT

A hemostatic clip device capable of being mounted to a surgical applicator and applied to a blood vessel so as to prevent blood flow. The clip device includes a pair of semi-rigid legs having free ends and opposed ends connected to a bridge. The legs are movable from an open mode in the applicator to a closed mode pinching the blood vessel. A plurality of first grooves are formed in parallel on one of the legs in a slanted direction relative to longitudinal dimension of the legs. A plurality of second grooves are formed in parallel on the other leg in a slanted direction relative the dimension of the legs approximately perpendicular to the second grooves so that the crimped vein remains stationary. A locking tab formed at the end of one of the legs is adapted to slide into a recess at the inner side of the opposed leg to prevent cross movement of the legs.

7 Claims, 7 Drawing Figures

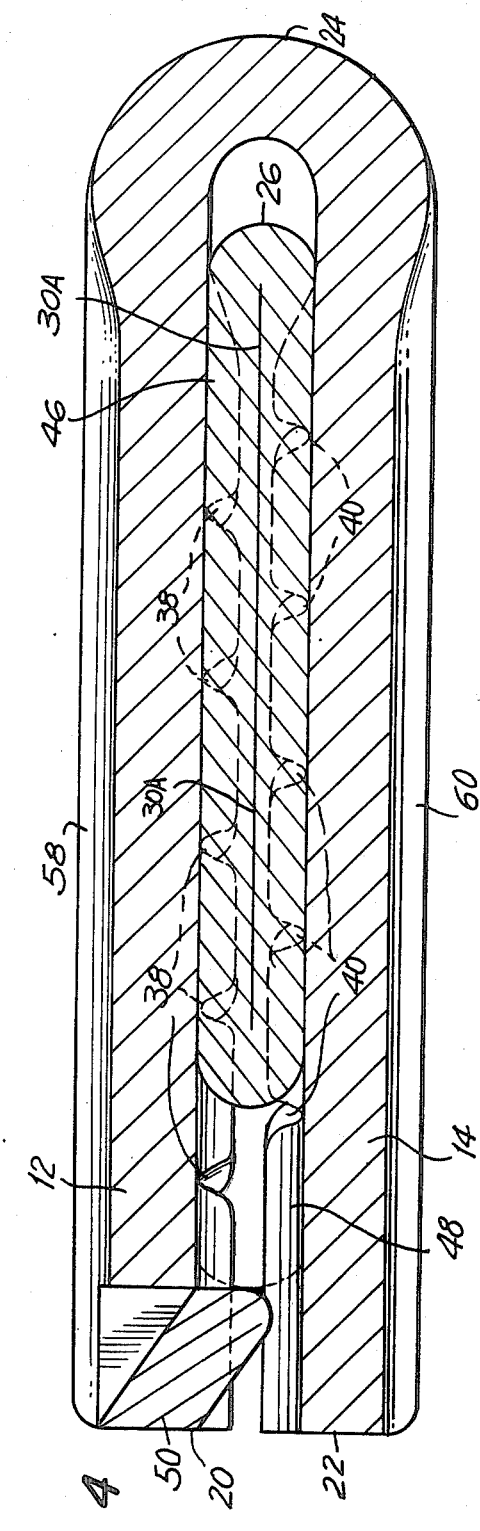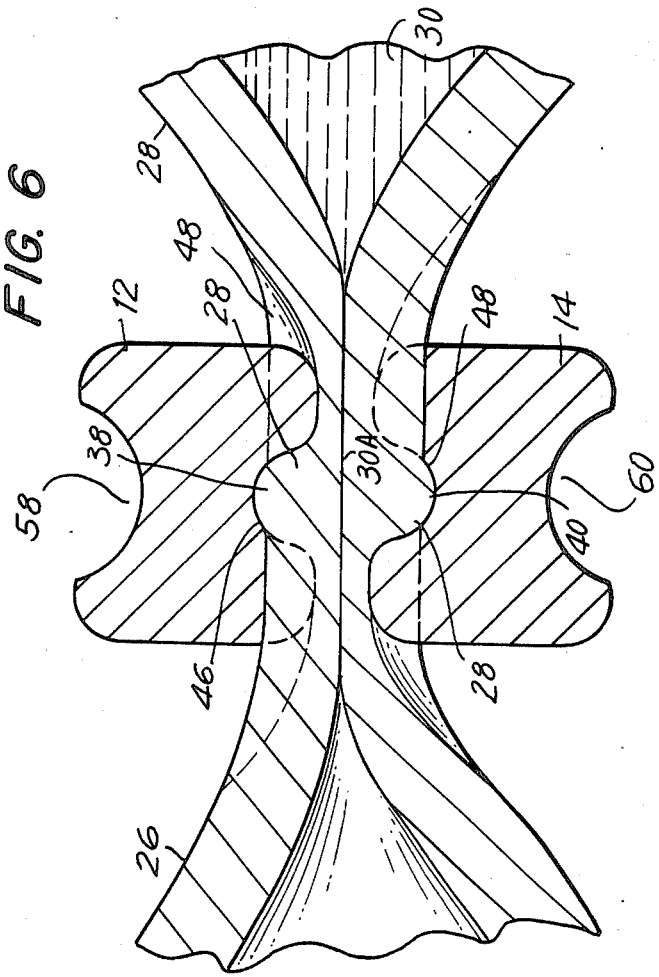

LIGATING CLIP

This invention relates to a surgical clip that is applied during a surgical procedure by means of a clip applicator and in particular to a hemostatic ligating clip.

In order to keep a wound of a patient free of blood during a surgical procedure such as an operation, blood vessels that have been severed in the area of the procedure must be occluded from passing blood. The method generally used presently is to crimp the open blood vessels with ligating clips that are applied by a surgeon by way of a forcepts applicator that contains one or a plurality of clips.

Ligating clips known in prior art have each of the facing inner surfaces of the opposed legs of the clips formed with spaced slanted grooves into which the walls of the blood vessel being crimped extend. Although the vessel is not as tightly pressed together at these grooves as at the more closely spaced surfaces of the arms free of grooves, nevertheless the vessel is prevented from sliding as it might if only the flat surfaces of the two legs were holding the walls of the vessel together. The walls of a blood vessel are smooth, and external forces tend to slide the vessel from its position in the crimp of the ligating clip.

Even though the grooves are employed to prevent sliding or movement of the blood vessel in the crimp, or, vice-versa, sliding of the clip along the vessel, the grooves are preferably angled relative the longitudinal, or lateral, extension of the legs of the clip. This construction prevents transverse sliding of the blood vessel between the crimping legs of the clip, or, vice-versa, lateral, sliding of the clip along the walls of the vessel. Thus, the angled grooves simultaneously serve to keep the vessel both from lateral and from transverse movement relative the clip.

A problem still remains with the anti-movement grooves used in the prior art, and that is the angle of inclination of all the grooves in the prior art are the same once the crimp has been made. That is, the grooves on both opposed surfaces of the crimping legs are, although angled relative the longitudinal lay of the clip, all the grooves are parallel with one another. The result is that relative the vessel the clip may yet slide, albeit neither laterally nor transversely, but angled relative both the lateral and transverse directions relative the legs of the clip.

Another problem exists in prior art hemostatic clips. The problem is that after the arms of the clip have been crimped around the blood vessel by the clip applicator, the two legs of the clip are subject to lateral movement relative one another about their effective pivot at the base of the crimped clip. Such cross-movement can result in loosening of the crimp or possibly tearing of the wall of the blood vessel.

Prior art relating to clip applicators is as follows:

U.S. Pat. No. 4,372,316 entitled "Surgical Device" issued to Blake and Kaufman, Feb. 8, 1983;

U.S. Pat. No. 4,296,751 entitled "Surgical Device" issued to Blake and Kaufman, Oct. 27, 1981;

U.S. Pat. No. 4,408,603 entitled "Surgical Device" issued to Blake and Kaufman, Oct. 11, 1983;

U.S. Pat. No. 4,523,707 entitled "Surgical Stapler" issued to Blake and Kaufman, June 18, 1985;

U.S. Pat. No. 4,372,316 entitled "Surgical Device" issued to Blake and Kaufman, Feb. 8, 1983;

Application No. 313,341, now U.S. Pat. No. 4,532,925 filed by Blake on Oct. 20, 1981 entitled "Ligator Device"; and Application No. 456,163, now U.S. Pat. No. 4,562,839 filed by Blake and entitled "Surgical Instrument".

SUMMARY OF THE INVENTION

Accordingly, it is an object of the present invention to provide a hemostatic ligating clip that prevents slippage between a blood vessel that has been crimped and the clip.

It is another object of the present invention to provide a hemostatic ligating clip that forms opposed angled grooves in the opposed inner surfaces of the legs of the clip when in the crimped position over the blood vessel so that both lateral and transverse movement between the clips and the vessel are inhibited.

It is yet a further object of the present invention to provide a hemostatic ligating clip that forms opposed angled grooves at the opposed surfaces of its crimping legs that are configured in crosses relative to one another when the clip is in the crimped position so that the vessel is doubly hindered at a series of positions from both lateral and transverse movements relative to the clip.

It is still another object of the present invention to provide a hemostatic ligating clip that is inhibited from having its crimping legs moving relative to one another and from any cross-movement of one leg relative to another so that the integrity of the crimp is maintained.

It is yet another object of the present invention to provide a hemostatic legating clip that has a locking projection extending from the inner surface of one leg that is positioned in one leg into a locking recess formed at the inner surface of the opposite leg in the crimping position so that the two legs are inhibited from cross-movement relative one another.

In order to achieve the above objects, as well as others that will become apparent hereafter, a hemostatic ligating clip device is provided for closing the tube of a blood vessel capable of being applied by a clip applicator. The clip device includes a pair of opposed, flexible, semi-rigid, elongated, first and second leg members having first and second connecting ends, opposed first and second free ends, and facing first and second inner sides, respectively. The first and second leg members extend in a longitudinal dimension between the first and second connecting ends and the first and second free ends, respectively. A flexible, semi-rigid bridge portion having opposed ends is connected to the first and second connecting ends. The leg members are spaced apart, to a closed mode wherein the clip device has been applied to the blood vessel and the leg members are separated by the wall of the blood vessel. The first and second leg members are in proximate association and positioned in the longitudinal dimension substantially transverse to the blood vessel. A plurality of first grooves are formed in the first leg member at the first side in parallel relationship at a first slant relative to the longitudinal dimension wherein the blood vessel is inhibited from sliding between the first and second leg members in a first direction transverse to the first slant. A plurality of second grooves are formed in the second leg member at the second side in parallel relationship at a second slant relative to the longitudinal direction wherein the blood vessel is inhibited from sliding between the leg members in a second direction transverse to the second slant. The first and second slants are generally in transverse relationship. The first and second grooves are positioned so as to cross each other along the longitudinal direction when the leg members are in the closed mode. The first and second grooves form crosses at approximate right angles. The longitudinal dimension includes a longitudinal midplane, the first and second grooves being at approximate symmetrical angles from the midplane. The first and second leg members form first and second inner channels respectively at the centers of the first and second facing sides along the longitudinal dimension. The first and second channels are in general opposed relationship when the leg members are in the closed mode. The blood vessel is spaced inwardly from the first and second free ends. The first leg member has a locking tab extending outwardly from the first channel at the first free end toward the second leg member. The second channel of the second leg member is adapted to receive the locking tab at the second free end, wherein in the closed mode the first and second leg members are prevented from cross-movement relative to one another and relative to the longitudinal dimension. The first and second leg members have first and second outer sides opposed to the first and second inner sides. The bridge member has an arcuate outer side joining the first and second outer sides. The first and second leg members form first and second outer channels at the center of the first and second outer sides that join to the arcuate outer side, whereby the outer channel is adapted to be held by the applicator when the first and second leg members are in the open mode to the closed mode. The bridge member has an arcuate inner side opposed to the arcuate outer side. The arcuate inner side forms a notch, whereby the bridge member is capable of being readily bent when the first and second leg members are moved from the open mode to the closed mode.

The present invention will be better understood and the objects and important features, other than those set forth above, will become apparent when consideration is given to the following details and description, which when taken in conjunction with the annexed drawings, describes, discloses, illustrates, and shows preferred embodiments or modifications of the present invention and what is presently considered and believed to be the best mode of practice in the principles thereof. Other embodiments or modifications may be suggested to those having the benefit of the teachings herein, and such other embodiments or modifications are intended to be reserved especially as they fall within the scope and spirit of the subjoined claims.

BRIEF DESCRIPTION OF THE DRAWINGS

FIG. 4 is a view taken through line 4—4 of FIG. 3;

FIG. 5 is a view taken through line 5—5 of FIG. 3;

FIG. 6 is a view taken through line 6—6 of FIG. 3; and

DESCRIPTION OF THE PREFERRED EMBODIMENT

Figure 1:
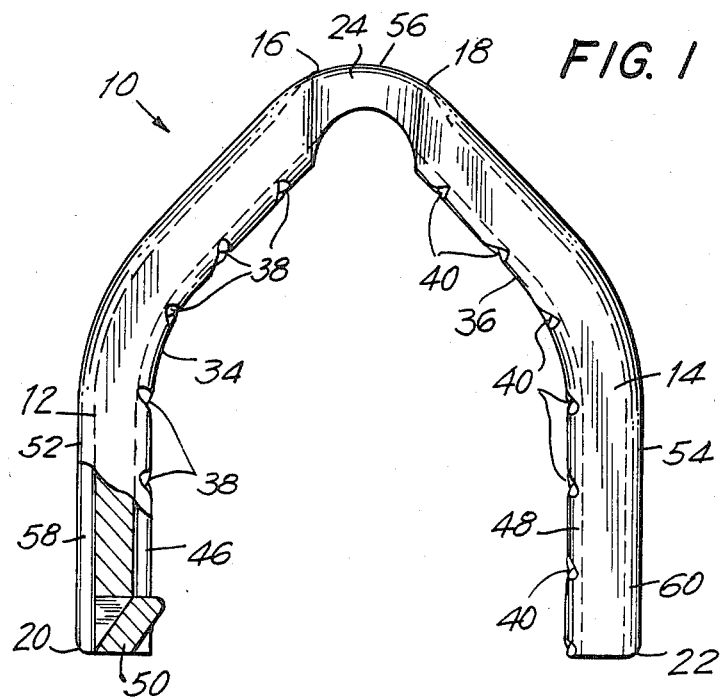
FIG. 1 is a partly stripped top view of the ligating clip in a pre-crimped mode.

Reference is now made specifically to the drawings in which identical or similar parts are designated by the same reference numerals throughout.

Figure 2:
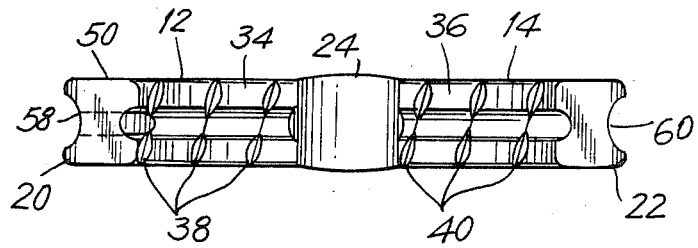
FIG. 2 is an end view of the clip taken from the leg ends in the pre-crimped mode.
Figure 3:
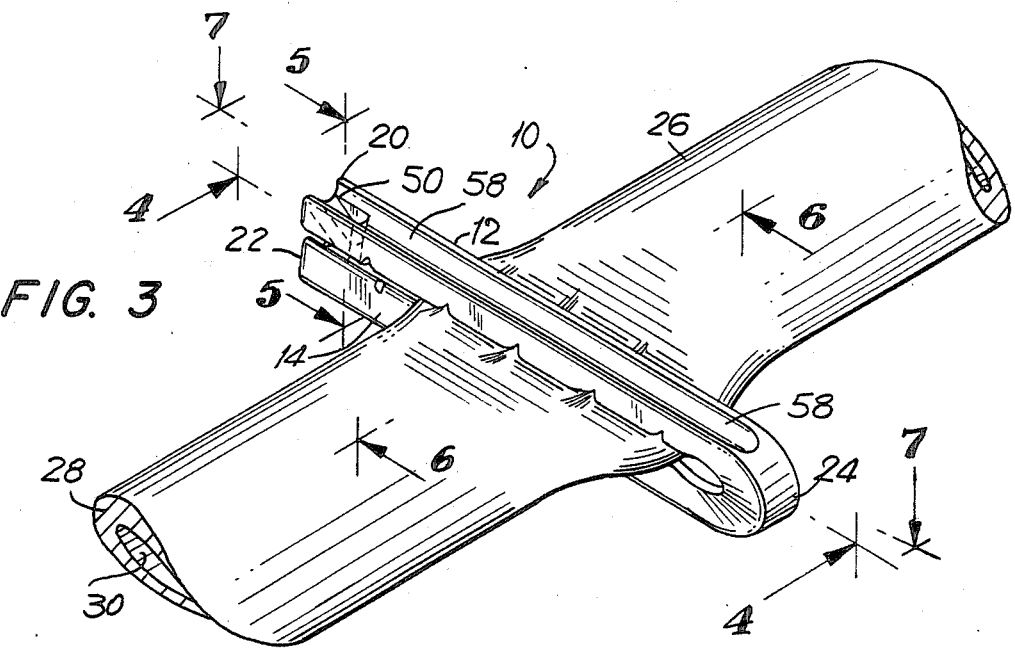
FIG. 3 is a perspective view of the clip taken in a crimping mode having pinched a blood vessel.

A hemostatic ligating clip indicated generally in FIG. 1 by numeral 10 includes a pair of generally opposed flexible leg members 12 and 14 having connecting ends 16 and 18, respectively. An arcuate flexible joining, or bridging, portion 24 has opposed ends connected to connecting end 16 and connecting end 18 so as to form clip 10 with leg members 12 and 14. FIGS. 1 and 2 illustrate the invention in its open mode, that is, the configuration it would have when mounted in a clip applicator (not shown) prior to use. FIGS. 3 through 8 illustrate clip 10 in its crimping, or closed, mode wherein leg members 12 and 14 have been forced closely together with the walls 28 of blood vessel 26 pinched between them so that the flow of blood through tube 30 formed by walls 28 has been occluded. The longitudinal, or lengthwise, dimension of clip device 10 and of leg members 12 and 14 extends between each free end 20 and 14 and each connecting end 16 and 18, respectively.

Clip device 10 and more specifically first and second leg members 12 and 14 are illustrated in an open mode in FIGS. 1 and 2 wherein clip device 10 is mounted in the clip applicator and leg members 12 and 14 are spaced apart. Clip device 10 is shown in FIG. 1 in the configuration of a Tudor arch so as to be capable of being slidably mounted on a matching clip holder of the applicator, but this configuration is for purposes of exposition only and can, of course, vary in accordance with the particular applicator being used.

From the open mode of FIGS. 1 and 2 clip device 10 and first and second leg members 12 and 14 are movable to a closed mode illustrated in FIGS. 3-7 wherein clip device 10 has been compressed by the clip activator around blood vessel 26 and leg members 12 and 14 have been pressed into proximate association and are separated only by wall 28 of vessel 26. Leg members 12 and 14 are positioned in the longitudinal dimension transverse to the lengthwise dimension of vessel 26, the lengthwise dimension being in general the direction of flow of blood in generally cylindrical vessel 26. Bridge member 24 has been bent in the closed mode so that leg members 12 and 14 can be proximately positioned. Tube 30 is seen in its closed position in FIGS. 5 and 6 by tube line 30A.

Figure 7:
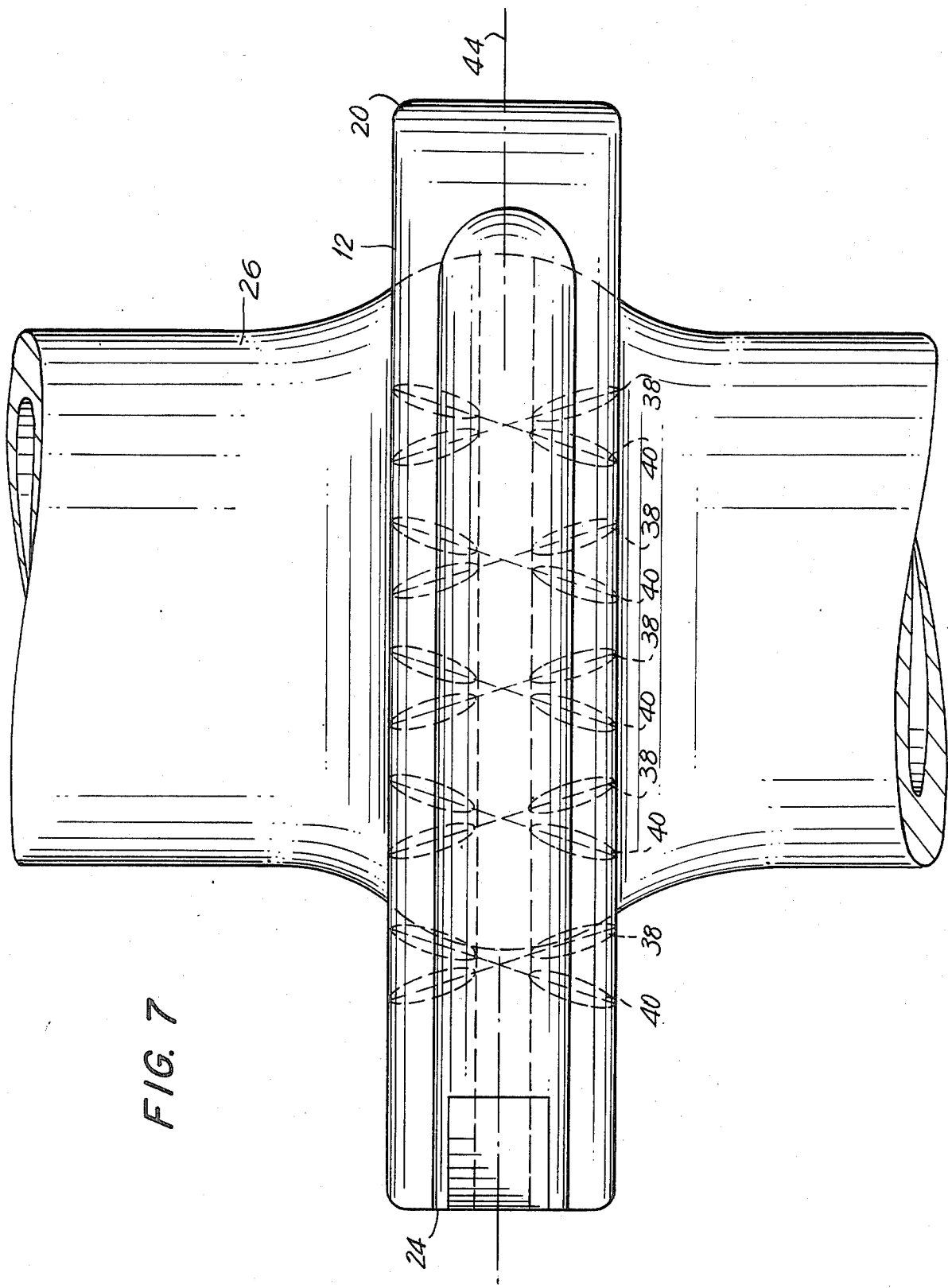
FIG. 7 is a view taken through line 7—7 of FIG. 3.

Leg members 12 and 14 include facing first and second inner sides 34 and 36, respectively. First leg member 12 forms a plurality of first grooves 38 at first inner side 34 in parallel relationship at a first slant relative to the longitudinal dimensions of legs 12 and 14 wherein blood vessel 26 is inhibited from sliding between first and second leg members 12 and 14 in a first direction transverse to the first slant. Second leg member 14 forms a plurality of second grooves 40 at second inner side 36 in parallel relationship at a second slant relative to the longitudinal dimension of legs 12 and 14 wherein blood vessel 26 is inhibited from sliding between leg members 12 and 14 in a second direction transverse to the second slant. The first and second slants of first and second grooves 38 and 40 are in transverse relationship. As seen in FIG. 7, first and second grooves 38 and 40 preferably form crosses 42, the crosses preferably being at approximate right angles. The longitudinal dimension of legs 12 and 14 includes a longitudininal midplane 44 that extends through the midsection of legs 12 and 14 in the closed mode seen in FIG. 7. The angles of first and second grooves 38 and 40 are preferably at approximate equal angles from midplane 44 so as to form a balanced cross configuration relative to midplane 44.

As seen best in FIGS. 5 and 6 but also in dotted lines in FIG. 1 and in FIG. 2, first and second leg members 12 and 14 form first and second inner channels 46 and 48, respectively, at the centers of first and second inner sides 34 and 36 along the longitudinal dimension. First and second inner channels 46 and 48 are in opposed relationship when leg members 12 and 14 are in the closed mode. Blood vessel 26 is spaced inwardly from free ends 20 and 22 of leg members 12 and 14, as seen in FIGS. 2 and 7. First leg member 12 has a projecting locking member, or tab 50 that extends outwardly from first inner channel 46 at first free end 20 toward second leg member 14. Second inner channel 48 is adapted to receive locking tab 50 at second free end 22. In the closed mode first and second leg members 12 and 14 are prevented from cross-movement relative to one another in the longitudinal dimension about bridge portion 24 as pivot area. First and second leg members 12 and 14 have first and second outer sides 52 and 54, respectively, opposed to first and second inner sides 34 and 36, respectively. Tab 50 is preferably formed by pinching the tab from first outer side 52 at first free end 20 inwardly past the lip of first inner channel 46 so that tab 50 will engage second inner channel 48.

Bridge member 24 has an arcuate outer side 56 that joins first and second outer sides 52 and 54. First and second leg members 12 and 14 and bridge member 24 form first and second outer channels 58 and 60 respectively at the center of first and second outer sides 52 and 54 and arcuate outer side 56. Outer channel 58 is shown to have an arcuate bottom side. Outer channel 58 is adapted to be held by the holder clip applicator during the time leg members 12 and 14 are in the open mode and during the time of movement of leg members 12 and 14 to the closed mode.

Bridge member 24 has an arcuate inner side opposite arcuate outer side 56. Bridge member 24 forms a notch 62 at the arcuate inner side so that flexible bridge member 24 is capable of being bent when leg members 12 and 14 are moved from their open mode to their closed mode.

Clip member 10 including leg members 12 and 14 and bridge member 24 can be designated as a wire clip. Clip member 10 is made of a flexible, semi-rigid metal, double annealed, and is capable of keeping its configuration once shaped when outer force is applied to it.

The embodiment of this invention particularly disclosed and described hereinabove is presented merely as an example of the invention. Other embodiments, forms, and modifications of the invention coming within the proper scope and spirit of the appended claims will, of course, readily suggest themselves to those skilled in the art.

What is claimed is:

1. A hemostatic ligating clip device for closing the tube of a blood vessel capable of being applied by a clip applicator, comprising, in combination, a pair of opposed, flexible, semi-rigid, elongated, first and second leg members having first and second connecting ends, opposed first and second free ends, and facing first and second inner sides, respectively, said first and second leg members extending in a longitudinal dimension between said first and second connecting ends and said first and second free ends, respectively, a flexible, semi-rigid bridge portion having opposed ends connected to said first and second connecting ends, said leg members being movable from an open mode wherein said clip device is mounted in said clip applicator and said leg members are spaced apart, to a closed mode wherein said clip device has been applied to said blood vessel and said leg members are separated by the wall of said blood vessel, said first and second leg members being in proximate association and positioned in said longitudinal dimension substantially transverse to said blood vessel, a plurality of first grooves formed in said first leg member at said first side in parallel relationship at a first slant relative to said longitudinal dimension wherein said blood vessel is inhibited from sliding between said first and second leg members in a first direction transverse to said first slant, a plurality of second grooves formed in said second leg member at said second side in parallel relationship at a second slant relative to said longitudinal direction wherein said blood vessel is inhibited from sliding between said leg members in a second direction transverse to said second slant, said first and second slants being generally in transverse relationship, and wherein said first and second leg members form first and second inner channels, respectively, at the centers of said first and second facing sides along said longitudinal dimension, said first and second channels being in general opposed relationship when said leg members are in said closed mode, said blood vessel being spaced inwardly from said first and second free ends, said first leg member having a locking tab extending outwardly from said first channel at said first free end toward said second leg member, said second channel of said second leg member being adapted to receive said locking tab at said second free end, wherein in said closed mode said first and second leg members are prevented from cross-movement relative to one another and relative to said longitudinal dimension.

2. The clip device according to claim 1, wherein said first and second grooves are positioned so as to cross each other along said longitudinal direction when said leg members are in said closed mode.

3. The clip device according to claim 2 wherein said first and second grooves form crosses at approximate right angles.

4. The clip device according to claim 3, wherein said longitudinal dimension includes a longitudinal midplane, said first and second grooves being at approximate 45 degree angles from said midplane.

5. The clip device according to claim 1, wherein said first and second leg members have first and second outer sides opposed to said first and second inner sides, said bridge member having an arcuate outer side joining said first and second outer sides, said first and second leg members forming first and second outer channels at the center of said first and second outer sides that join to said arcuate outer side, whereby said outer channel is adapted to be held by said applicator when said first and second leg members are in said open mode and during the time of moving said first and second leg members from said open mode to said closed mode.

6. The clip device according to claim 5, wherein said bridge member has an arcuate inner side opposed to said arcuate outer side, said arcuate inner side forming a notch, whereby said bridge member is capale of being readily bent when said first and second leg members are moved from said open mode to said closed mode.

7. The clip device according to claim 1, wherein said clip device is made of metal.

* * * * *